(12) United States Patent
Heuer et al.

(10) Patent No.: US 8,546,369 B2
(45) Date of Patent: *Oct. 1, 2013

(54) SALTS OF CREATINE IMINO SUGAR AMIDES

(75) Inventors: Marvin Heuer, Oakville (CA); Michele Molino, Oakville (CA); Joseph MacDougall, Oakville (CA)

(73) Assignee: Northern Innovations Holding Corp., Oakdale (CA)

( * ) Notice: Subject to any disclaimer, the term of this patent is extended or adjusted under 35 U.S.C. 154(b) by 976 days.

This patent is subject to a terminal disclaimer.

(21) Appl. No.: 12/229,955

(22) Filed: Aug. 28, 2008

(65) Prior Publication Data

US 2009/0298877 A1 Dec. 3, 2009

Related U.S. Application Data

(60) Provisional application No. 61/059,938, filed on Jun. 9, 2008, provisional application No. 61/057,539, filed on May 30, 2008, provisional application No. 61/057,521, filed on May 30, 2008, provisional application No. 61/057,509, filed on May 30, 2008, provisional application No. 61/507,489, filed on May 30, 2008, provisional application No. 61/507,469, filed on May 30, 2008.

(51) Int. Cl.
*A61K 31/33* (2006.01)
*A61K 31/435* (2006.01)
*A61K 31/155* (2006.01)

(52) U.S. Cl.
USPC ............................ 514/183; 514/277; 514/634

(58) Field of Classification Search
USPC .................................. 514/188, 277, 634, 183
See application file for complete search history.

(56) References Cited

U.S. PATENT DOCUMENTS

| | | | |
|---|---|---|---|
| 5,561,146 A * | 10/1996 | Kim et al. | .................... 514/13.7 |
| 5,886,040 A | 3/1999 | Fang | |
| 5,973,199 A | 10/1999 | Negrisoli et al. | |
| 6,166,249 A | 12/2000 | Pischel et al. | |
| 6,211,407 B1 | 4/2001 | Thomson | |
| 6,838,562 B2 | 1/2005 | Abraham et al. | |
| 6,897,334 B2 | 5/2005 | Vennerstrom | |
| 7,109,373 B2 | 9/2006 | Boldt | |
| 2004/0029969 A1 | 2/2004 | Blatt et al. | |
| 2004/0120983 A1 | 6/2004 | Connolly | |
| 2006/0269535 A1 | 11/2006 | Naidu et al. | |

FOREIGN PATENT DOCUMENTS

WO    WO-00/40217 A1    7/2000

OTHER PUBLICATIONS

Harris RC, et al. Elevation of creatine in resting and exercised muscle of normal subjects by creatine supplementation. Clin Sci (Lond). Sep. 1992;83(3):367-74.
Greenhaff PL, et al. Effect of oral creatine supplementation on skeletal muscle phosphocreatine resynthesis. Am J Physiol. May 1994;266(5 Pt 1):E725-30.
Greenhaff PL, et al. Influence of oral creatine supplementation of muscle torque during repeated bouts on maximal voluntary exercise in man. Clin Sci (Lond). May 1993;84(5):565-71.
Olsen S, et al. Creatine supplementation augments the increase in satellite cell and myonuclei number in human skeletal muscle induced by strength training. J Physiol. Jun. 2006;573(Pt 2):525-34.
Zammit PS, et al. The Skeletal Muscle Satellite Cell: The Stem Cell That Came in From the Cold. J Histochem Cytochem. Aug. 2006; 54(11):1177-91.
Sartorelli V, et al. Molecular and cellular determinants of skeletal muscle atropy and hypertropy. Sci STKE. Jul. 2004;2004(244):re11.
Mellor R, et al. Cellular effects of deoxynojirimycin analogues: uptake, retention and inhibition of glycoshingolipid biosynthesis. Biochem J. Aug. 1, 2004;381(Pt 3):861-6.
Asano N, et al. N-containing sugars from Morus alba and their glycosidase inhibitory activities. Carbohydr Res. Jun. 17, 1994;259(2):243-55.
Yoshikuni Y, et al. inhibition of intestinal alpha-glucosidase and postprandial hyperglycemia by N-substituted moranoline derivatives. J Pharmacobiodyn. May 1988;11(5):356-62.

* cited by examiner

*Primary Examiner* — Sreeni Padmanabhan
*Assistant Examiner* — Shobha Kantamneni

(57) ABSTRACT

The present invention relates to stable salts of creatine imino sugar amides and an inorganic or organic acid endowed with enhanced nutritional and/or therapeutical efficacy in respect to their individual effects and to solid compositions containing such salts, particularly suited to oral and parenteral administration. Methods of preparation and use of these compositions are also provided.

10 Claims, No Drawings

SALTS OF CREATINE IMINO SUGAR AMIDES

RELATED APPLICATIONS

The present application is related to and claims benefit of priority to U.S. Provisional Application No. 61/059,938 entitled "Salts of Creatine Imino Sugar Amides" filed Jun. 9, 2008, the disclosure of which is hereby fully incorporated by reference; and 61/057,539, U.S. Provisional Application No. 61/057,521, U.S. Provisional Application No. 61/057,509, U.S. Provisional Application No. 61/057,489, and U.S. Provisional Application No. 61/057,469, all of which were filed May 30, 2008, the disclosure of which are all hereby fully incorporated by reference. Additionally, the instant application is related to the applicant's co-pending U.S. patent application Ser. No. 12/229,979, entitled "Preparations containing Creatine and Imino Sugars" filed on this same day, herein fully incorporated by reference.

FIELD OF THE INVENTION

The present invention relates to structures, methods for producing, and solid compositions of stable salts of creatine imino sugar amides. More specifically, formed salts of the present invention are particularly well suited for oral and parenteral administration. The formed salts may provide enhanced nutritional and/or therapeutical efficacy in relation to the individual components alone.

BACKGROUND OF THE INVENTION

Creatine is a naturally occurring amino acid that is derived from the amino acids; glycine, arginine and methionine. Although it is ingested from meats and fish, the human body also synthesizes its own creatine. About 65% of creatine is stored in the musculature of mammals in the form of phosphocreatine (creatine bound to a phosphate molecule), and utilized mostly as a source of energy for muscle. Oral supplementation of creatine has been shown to increase creatine concentration in muscle, and also enables an increase in the resynthesis of phosphocreatine, resulting in a rapid replenishment of ATP within the first two minutes of the start of exercise.

The beneficial effects of creatine supplementation with regard to skeletal muscle are apparently not restricted to the role of creatine in energy metabolism. Creatine supplementation in combination with strength training results in specific, measurable physiological changes in skeletal muscle compared to strength training alone. For example, creatine supplementation amplifies the strength training-induced increase of human skeletal satellite cells as well as the number of myonuclei in human skeletal muscle fibers. Satellite cells, stem cells of adult muscle, are normally in a quiescent state and become activated to fulfill roles of routine maintenance, repair and hypertrophy. Postnatal muscle growth involves both myofiber hypertrophy and increased numbers of myonuclei—the source of which are satellite cells.

Imino sugars constitute a major class of naturally occurring molecules that have important and diverse biological functions. Imino sugars may be pentose, hexose or heptose sugars where at least one oxygen-containing group is replaced by a nitrogen-containing group. These imino sugars are useful in pharmacology, since they have been found to play major roles in the selective inhibition of various enzymatic functions.

SUMMARY OF THE INVENTION

In the present invention, creatine imino sugar amide salts, methods for their production, and solid compositions comprising said creatine imino sugar amide salts, are disclosed. Specifically, the creatine imino sugar amide salts comprise an acceptable inorganic or organic acid and a creatine imino sugar amide. In the present invention, the compounds comprise salts of an imino sugar bound to creatine, via an amide linkage, and having a structure corresponding to Formula 1:

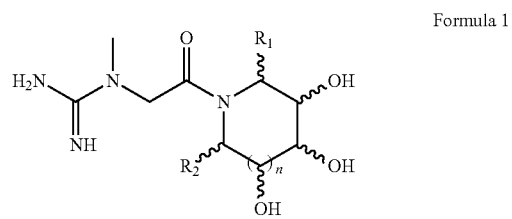

Formula 1 where
$R_1$=H, OH, or $CH_2OH$;
$R_2$=H, OH, $CH_3$ or $CH_2OH$; and
n=0, 1 or 2.

An additional aspect of the present invention discloses a method for producing creatine imino sugar amide salts.

In a further aspect of the present invention, the creatine imino sugar amide salts may be combined with one or more pharmaceutically acceptable carriers to form a nutritional composition, which can be administered to a subject.

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards the structures, synthesis and solid compositions of stable salts of creatine imino sugar amides.

The present invention provides for the production of stable salts, which may afford a combination of creatine imino sugar amides and an inorganic or organic acid, free of physiologically unsafe additives to an individual upon administration to said individual. Furthermore, the present invention is particularly well suited for use in tablets, capsules, powders, granules, powdered beverage mixes and other forms known in the art of dietary supplements.

As used herein, 'creatine' refers to the chemical N-methyl-N-guanyl Glycine, (CAS Registry No. 57-00-1), also known as, (alpha-methyl guanido) acetic acid, N-(aminoiminomethyl)-N-glycine, Methylglycocyamine, Methylguanidoacetic Acid, or N-Methyl-N-guanylglycine. Additionally, as used herein, 'creatine' also includes derivatives of creatine such as esters and salts.

As used herein, 'deoxynojirimycin' refers to the chemical (2R,3R,4R,5S)-2-(hydroxymethyl)-3,4,5-piperideinetriol, (CAS Registry No. 19130-96-2), also known as D-5-amino-1,5-dideoxyglucopyranose, 1,5-dideoxy-1,5-imino-D-glucitol, (2R,3R,4R,5S)-2-hydroxymethyl-3,4,5-trihydroxypiperidine, or moranoline. Additionally, as used herein, 'deoxynojirimycin' also includes derivatives of deoxynojirimycin such as esters and salts.

As used herein, 'deoxygalactonojirimycin' refers to the chemical 2-(hydroxymethyl)piperidine-3,4,5-triol, (CAS Registry No. 75172-81-5), also known as 1,5-dideoxy-1,5-imino-D-galactitol, or galactostatin. Additionally, as used here, 'deoxygalactonojirimycin' also includes derivatives of deoxygalactonojirimycin such as esters and salts.

As used herein, 'deoxymannojirimycin' refers to the chemical (2R,3R,4R,5R)-2-(hydroxymethyl)piperidine-3,4,5-triol, (CAS Registry No. 7346543-7), also known as 1,5-dideoxy-1,5-imino-D-mannitol. Additionally, as used here, 'deoxymannojirimycin' also includes derivatives of deoxymannojirimycin such as esters and salts.

As used herein, 'homomannojirimycin' refers to the chemical (2R,3R,5R,6R)-2,6-bis(hydroxymethyl)piperidine-3,4,5-triol, (CAS Registry No. 127995-29-3). Additionally, as used here, 'homomannojirimycin' also includes derivatives of homomannojirimycin such as esters and salts.

As used herein, 'homonojirimycin' refers to the chemical (2R,3R,5S,6R)-2,6-bis(hydroxymethyl)piperidine-3,4,5-triol, (CAS Registry No. 119557-99-2). Additionally, as used here, 'homonojirimycin' also includes derivatives of homonojirimycin such as esters and salts.

As used herein, 'citric acid' refers to the chemical 2-hydroxy-1,2,3-propane-tricarboxylic acid, (CAS Registry No. 77-92-9), also known as, β-hydroxytricarboxylic acid. Additionally, as used herein, 'citric acid' also includes derivatives of citrate such as esters, amides, and salts, as well as other derivatives, including derivatives having pharmacoproperties upon metabolism to an active form.

As used herein, 'maleic acid' refers to the chemical (Z)-butenedioic acid, (CAS registry No. 110-16-7), also known as toxilic acid, cis-1,2-ethylenedicarboxylic acid. Additionally, as used herein, 'maleic acid' also includes derivatives of maleic acid such as esters, amides, and salts, as well as other derivatives, including derivatives having pharmacoproperties upon metabolism to an active form.

As used herein, 'malic acid' refers to the chemical 1-Hydroxy-1,2-ethanedicarboxylic acid, (CAS Registry No. 6915-15-17), also known as, hydroxybutanedioic acid, hydroxysuccinic acid, malate, or 2-hydroxybutanedioate. Additionally, as used herein, 'malic acid' also includes derivatives of malate such as esters, amides, and salts, as well as other derivatives, including derivatives having pharmacoproperties upon metabolism to an active form.

As used herein, 'fumaric acid' refers to the chemical (E)-2-butenedioic acid, (CAS Registry No. 110-17-8), also known as, trans-1,2-ethylenedicarboxylic acid, allomaleic acid, and boletic acid. Additionally, as used herein, 'fumaric acid' also includes derivatives of fumarate such as esters, amides, and salts, as well as other derivatives, including derivatives having pharmacoproperties upon metabolism to an active form.

As used herein, the term 'organic acid' refers to organic compounds which contain carboxylic acids (—C(O)OH). Typical examples of organic acids include, but are not limited to; malic acid, fumaric acid, citric acid, orotic acid, lactic acid, pyruvic acid, and tartaric acid.

As used herein, the term 'subject' refers to mammals and non-mammals. Mammals refers to any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

As used here, the term 'acceptable oral dosage form' would be known by one of skill in the art to include, for example, powder beverage mixes, liquid beverages, ready-to-eat bars, capsules, liquid capsules, tablets, caplets, dietary gels, Soft-gel™ caplets, and gel-caps.

As used here, the term 'parenteral' refers to methods of administration of nutrients to that region outside of the digestive tract. Examples of parenteral routes of administration include, but are not limited to, subcutaneous, intramuscular or intravenous injection, and nasopharyngeal, mucosal or transdermal absorption.

As used herein, the term 'pharmaceutically-acceptable salt' refers to acid-addition salts of creatine imino sugar amides with an inorganic or organic acid such as hydrochloric, hydrobromic, sulphuric, trifluoroacetic, citric, maleic, malic, or fumaric acid.

The term 'pharmaceutically acceptable carrier' is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be 'acceptable' in the sense of being compatible with the subject composition and its components and not injurious to the individual to which it is administered. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; and (15) other non-toxic compatible substances employed in pharmaceutical formulations, and combinations thereof.

As used herein, the term 'nutritional composition' includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, 'nutritional compositions' as disclosed herein belong to category of compositions having at least one physiological function when administered to a subject by conventional routes of administration.

Alternatively, formulations and nutritional compositions belonging to the present invention may be considered to be nutraceuticals. As used herein, the term 'nutraceutical' is recognized and used in the art to describe a specific chemical compound or combination of compounds found in, organic matter for example, which may prevent, ameliorate or otherwise confer benefits against an undesirable condition. As is known in the art, the term 'nutraceutical' is used to refer any substance that is a food, a part of food, or an extract of food which is suitable for consumption by an individual and providing physiological benefit which may be medical or health-related. Furthermore, the term has been used to refer to a product isolated, extracted or purified from foods or naturally-derived material suitable for consumption by an individual and usually sold in medicinal forms, such as caplets, tablet, capsules, Soft-gel™ caplets, gel-caps and the like, not associated with food.

Compounds of an imino sugar and a creatine bound via an amide bond offer increased resistance to the cyclization of creatine while in solution. It is commonly understood that hydrolysis of amides is more difficult to accomplish than the hydrolysis of esters. While amides of creatine and an imino sugar would be more stable in solution than related esters, the salts of these amides of creatine and an imino sugar would offer the further advantage of enhanced nutritional and/or therapeutical efficacy due to increased solubility.

According to the present invention, the compounds disclosed herein comprise compounds of creatine imino sugar amides combined with an inorganic or organic acid to form a creatine imino sugar amide salts. The creatine imino sugar amide salts can be prepared according to the details set forth in the description below.

In one step of the process, a creatine imino sugar amide is dissolved in an excess of hot lower alcohol. The lower alcohol is considered to be hot, as would be known by one of ordinary skill in the art. Preferably the lower alcohol is considered to be hot when heated to a temperature about 5° C. below the boiling point of the corresponding lower alcohol.

In various embodiments of the present invention, the creatine imino sugar amide may be selected, for example, from the group including of 1-methyl-1-(2-oxo-2-((2R,3R,4R,5S)-3,4,5-trihydroxy-2-(hydroxymethyl)piperidin-1-yl) ethyl)guanidine, also known as creatine deoxynojirimycin amide; 1-methyl-1-(2-oxo-2-((3S,4R,5S)-3,4,5-trihydroxy-2-(hydroxymethyl)piperidin-1-yl)ethyl)guanidine, also known as creatine deoxygalactonojirimycin amide; 1-methyl-1-(2-oxo-2-((2R,3R,4R,5R)-3,4,5-trihydroxy-2-(hydroxymethyl)piperidin-1-yl)ethyl)guanidine, also known as creatine deoxymannojirimycin amide; 1-methyl-1-(2-oxo-2-((2R,3R,5R,6R)-3,4,5-trihydroxy-2,6-bis(hydroxymethyl)piperidin-1-yl)ethyl)guanidine, also known as creatine homomannojirimycin amide; and 1-methyl-1-(2-oxo-2-((2R,3R,4S,5S,6R)-3,4,5-trihydroxy-2,6-bis(hydroxymethyl)piperidin-1-yl)ethyl)guanidine, also known as creatine homonojirimycin amide. However, it should be noted that a creatine imino sugar amine may be made with any imino sugar as would be known by one of skill in the art, and would be acceptable for use in the present invention.

Additionally, in various embodiments of the present invention, the lower alcohol preferably is selected from the group consisting of methanol, ethanol, propanol, and isopropanol. These lower alcohols may be used singly or in admixture containing two or more alcohols.

In another step of the process, the inorganic or organic acid is dissolved in an excess of hot lower alcohol. The lower alcohol is considered to be hot, as would be known by one of ordinary skill in the art. Preferably the lower alcohol is considered to be hot when heated to a temperature about 5° C. below the boiling point of the corresponding lower alcohol.

In various embodiments of the present invention, the inorganic or organic acid preferably is selected from the group consisting of hydrochloric acid, hydrobromic acid, sulphuric acid, trifluoroacetic acid, citric acid, maleic acid, malic acid and fumaric acid.

The order in which the creatine imino sugar amide and the inorganic or organic acid are dissolved is not critical. Both solutions prepared above are then mixed together and heated to about the boiling point of the corresponding lower alcohol. If there are solids still present after heating, the combined solution is filtered while hot to remove any unreacted starting materials. The combined solution is then allowed to cool to room temperature, covered and refrigerated or cooled until crystallization occurs, preferably for between about 24 to about 48 hours. The resultant solid is filtered under vacuum and washed with ice cold lower alcohol, yielding the creatine imino sugar amide salt.

In larger scale preparations of the present invention, diethyl ether can be added until the cloud point, as would be known to one of skill in the art, is reached after the mixture is cooled to room temperature, after which the solution is refrigerated or cooled to allow crystallization to complete. This will facilitate greater precipitation of the product thus yielding more of the creatine imino sugar amide salt, which would be desired in industrial settings.

Creatine imino sugar amide salts are used advantageously alone or with additional active ingredients, such as, trace elements, vitamins, mineral substances, or other amino acids as well as, optionally, excipients usually used for the preparation of the respective forms of administration. The forms of administration include, particularly, all varieties of tablets, both those that are swallowed without being chewed, and tablets to be chewed or dissolved in the mouth of an individual, as well as those that are dissolved in a liquid before being ingested by an individual. The tablet forms include uncoated tablets, one-layer or multilayer or encased forms or effervescent tablets. Further preferred forms of administration are capsules of hard and soft gelatin, the latter being particularly suitable to include a liquid core. Additionally, creatine imino sugar amide salts can be used advantageously for the preparation of solutions and suspensions and as a powder, either effervescent or granulated.

Creatine imino sugar amide salts of the present invention may, for example include:

1. 1-methyl-1-(2-oxo-2-((2R,3R,4R,5S)-3,4,5-trihydroxy-2-(hydroxymethyl)piperidin-1-yl)ethyl)guanidine hydrochloride;
2. 1-methyl-1-(2-oxo-2-((2R,3R,4R,5S)-3,4,5-trihydroxy-2-(hydroxymethyl)piperidin-1-yl)ethyl)guanidine hydrobromide;
3. 1-methyl-1-(2-oxo-2-((2R,3R,4R,5S)-3,4,5-trihydroxy-2-(hydroxymethyl)piperidin-1-yl)ethyl)guanidine sulfate;
4. 1-methyl-1-(2-oxo-2-((2R,3R,4R,5S)-3,4,5-trihydroxy-2-(hydroxymethyl)piperidin-1-yl)ethyl)guanidine hemisulfate;
5. 1-methyl-1-(2-oxo-2-((2R,3R,4R,5S)-3,4,5-trihydroxy-2-(hydroxymethyl)piperidin-1-yl)ethyl)guanidine 2,2,2-trifluoroacetate;
6. 1-methyl-1-(2-oxo-2-((2R,3R,4R,5S)-3,4,5-trihydroxy-2-(hydroxy-methyl)piperidin-1-yl)ethyl)guanidine-2-hydroxypropane-1,2,3-tricarboxylate;
7. 1-methyl-1-(2-oxo-2-((2R,3R,4R,5S)-3,4,5-trihydroxy-2-(hydroxy-methyl)piperidin-1-yl)ethyl)guanidine-hemi(2-hydroxypropane-1,2,3-tricarboxylate);
8. tris(1-methyl-1-(2-oxo-2-((2R,3R,4R,5S)-3,4,5-trihydroxy-2-(hydroxy-methyl)piperidin-1-yl)ethyl)guanidine)-2-hydroxypropane-1,2,3-tricarboxylate;
9. 1-methyl-1-(2-oxo-2-((2R,3R,4R,5S)-3,4,5-trihydroxy-2-(hydroxymethyl)piperidin-1-yl)ethyl)guanidine maleate;
10. 1-methyl-1-(2-oxo-2-((2R,3R,4R,5S)-3,4,5-trihydroxy-2-(hydroxymethyl)piperidin-1-yl)ethyl)guanidine hemimaleate;
11. 1-methyl-1-(2-oxo-2-((2R,3R,4R,5S)-3,4,5-trihydroxy-2-(hydroxymethyl)piperidin-1-yl)ethyl)guanidine malate;
12. 1-methyl-1-(2-oxo-2-((2R,3R,4R,5S)-3,4,5-trihydroxy-2-(hydroxymethyl)piperidin-1-yl)ethyl)guanidine hemimalate;
13. 1-methyl-1-(2-oxo-2-((2R,3R,4R,5S)-3,4,5-trihydroxy-2-(hydroxymethyl)piperidin-1-yl)ethyl)guanidine fumarate;
14. 1-methyl-1-(2-oxo-2-((2R,3R,4R,5S)-3,4,5-trihydroxy-2-(hydroxymethyl)piperidin-1-yl)ethyl)guanidine hemifumarate;

15. 1-methyl-1-(2-oxo-2-((3S,4R,5S)-3,4,5-trihydroxy-2-(hydroxymethyl)piperidin-1-yl)ethyl)guanidine hydrochloride;
16. 1-methyl-1-(2-oxo-2-((3S,4R,5S)-3,4,5-trihydroxy-2-(hydroxy-methyl)piperidin-1-yl)ethyl)guanidine hydrobromide;
17. 1-methyl-1-(2-oxo-2-((3S,4R,5S)-3,4,5-trihydroxy-2-(hydroxy-methyl)piperidin-1-yl)ethyl)guanidine sulfate;
18. 1-methyl-1-(2-oxo-2-((3S,4R,5S)-3,4,5-trihydroxy-2-(hydroxymethyl)piperidin-1-yl)ethyl)guanidine hemisulfate;
19. 1-methyl-1-(2-oxo-2-((3S,4R,5S)-3,4,5-trihydroxy-2-(hydroxymethyl)piperidin-1-yl)ethyl)guanidine 2,2,2-trifluoroacetate;
20. 1-methyl-1-(2-oxo-2-((3S,4R,5S)-3,4,5-trihydroxy-2-(hydroxy-methyl)piperidin-1-yl)ethyl)guanidine-2-hydroxypropane-1,2,3-tricarboxylate;
21. 1-methyl-1-(2-oxo-2-((3S,4R,5S)-3,4,5-trihydroxy-2-(hydroxy-methyl)piperidin-1-yl)ethyl)guanidine-hemi(2-hydroxypropane-1,2,3-tricarboxylate);
22. tris(1-methyl-1-(2-oxo-2-((3S,4R,5S)-3,4,5-trihydroxy-2-(hydroxy-methyl)piperidin-1-yl)ethyl)guanidine)-2-hydroxypropane-1,2,3-tricarboxylate;
23. 1-methyl-1-(2-oxo-2-((3S,4R,5S)-3,4,5-trihydroxy-2-(hydroxymethyl)piperidin-1-yl)ethyl)guanidine maleate;
24. 1-methyl-1-(2-oxo-2-((3S,4R,5S)-3,4,5-trihydroxy-2-(hydroxymethyl)piperidin-1-yl)ethyl)guanidine hemimaleate;
25. 1-methyl-1-(2-oxo-2-((3S,4R,5S)-3,4,5-trihydroxy-2-(hydroxymethyl)piperidin-1-yl)ethyl)guanidine malate;
26. 1-methyl-1-(2-oxo-2-((3S,4R,5S)-3,4,5-trihydroxy-2-(hydroxymethyl)piperidin-1-yl)ethyl)guanidine hemimalate;
27. 1-methyl-1-(2-oxo-2-((3S,4R,5S)-3,4,5-trihydroxy-2-(hydroxymethyl)piperidin-1-yl)ethyl)guanidine fumarate;
28. 1-methyl-1-(2-oxo-2-((3S,4R,5S)-3,4,5-trihydroxy-2-(hydroxymethyl)piperidin-1-yl)ethyl)guanidine hemifumarate;
29. 1-methyl-1-(2-oxo-2-((2R,3R,4R,5R)-3,4,5-trihydroxy-2-(hydroxymethyl)piperidin-1-yl)ethyl)guanidine hydrochloride;
30. 1-methyl-1-(2-oxo-2-((2R,3R,4R,5R)-3,4,5-trihydroxy-2-(hydroxymethyl)piperidin-1-yl)ethyl)guanidine hydrobromide;
31. 1-methyl-1-(2-oxo-2-((2R,3R,4R,5R)-3,4,5-trihydroxy-2-(hydroxymethyl)piperidin-1-yl)ethyl)guanidine sulfate;
32. 1-methyl-1-(2-oxo-2-((2R,3R,4R,5R)-3,4,5-trihydroxy-2-(hydroxymethyl)piperidin-1-yl)ethyl)guanidine hemisulfate;
33. 1-methyl-1-(2-oxo-2-((2R,3R,4R,5R)-3,4,5-trihydroxy-2-(hydroxymethyl)piperidin-1-yl)ethyl)guanidine 2,2,2-trifluoroacetate;
34. 1-methyl-1-(2-oxo-2-((2R,3R,4R,5R)-3,4,5-trihydroxy-2-(hydroxy-methyl)piperidin-1-yl)ethyl)guanidine-2-hydroxypropane-1,2,3-tricarboxylate;
35. 1-methyl-1-(2-oxo-2-((2R,3R,4R,5R)-3,4,5-trihydroxy-2-(hydroxy-methyl)piperidin-1-yl)ethyl)guanidine-hemi(2-hydroxypropane-1,2,3-tricarboxylate);
36. tris(1-methyl-1-(2-oxo-2-((2R,3R,4R,5R)-3,4,5-trihydroxy-2-(hydroxy-methyl)piperidin-1-yl)ethyl)guanidine)-2-hydroxypropane-1,2,3-tricarboxylate;
37. 1-methyl-1-(2-oxo-2-((2R,3R,4R,5R)-3,4,5-trihydroxy-2-(hydroxymethyl)piperidin-1-yl)ethyl)guanidine maleate;
38. 1-methyl-1-(2-oxo-2-((2R,3R,4R,5R)-3,4,5-trihydroxy-2-(hydroxymethyl)piperidin-1-yl)ethyl)guanidine hemimaleate;
39. 1-methyl-1-(2-oxo-2-((2R,3R,4R,5R)-3,4,5-trihydroxy-2-(hydroxymethyl)piperidin-1-yl)ethyl)guanidine malate;
40. 1-methyl-1-(2-oxo-2-((2R,3R,4R,5R)-3,4,5-trihydroxy-2-(hydroxymethyl)piperidin-1-yl)ethyl)guanidine hemimalate;
41. 1-methyl-1-(2-oxo-2-((2R,3R,4R,5R)-3,4,5-trihydroxy-2-(hydroxymethyl)piperidin-1-yl)ethyl)guanidine fumarate;
42. 1-methyl-1-(2-oxo-2-((2R,3R,4R,5R)-3,4,5-trihydroxy-2-(hydroxymethyl)piperidin-1-yl)ethyl)guanidine hemifumarate;
43. 1-methyl-1-(2-oxo-2-((2R,3R,5R,6R)-3,4,5-trihydroxy-2,6-bis(hydroxymethyl)piperidin-1-yl)ethyl)guanidine hydrochloride;
44. 1-methyl-1-(2-oxo-2-((2R,3R,5R,6R)-3,4,5-trihydroxy-2,6-bis(hydroxymethyl)piperidin-1-yl)ethyl)guanidine hydrobromide;
45. 1-methyl-1-(2-oxo-2-((2R,3R,5R,6R)-3,4,5-trihydroxy-2,6-bis(hydroxymethyl)piperidin-1-yl)ethyl)guanidine sulfate;
46. 1-methyl-1-(2-oxo-2-((2R,3R,5R,6R)-3,4,5-trihydroxy-2,6-bis(hydroxymethyl)piperidin-1-yl)ethyl)guanidine hemisulfate;
47. 1-methyl-1-(2-oxo-2-((2R,3R,5R,6R)-3,4,5-trihydroxy-2,6-bis(hydroxymethyl)piperidin-1-yl)ethyl)guanidine 2,2,2-trifluoroacetate;
48. 1-methyl-1-(2-oxo-2-((2R,3R,5R,6R)-3,4,5-trihydroxy-2,6-bis(hydroxymethyl)piperidin-1-yl)ethyl)guanidine-2-hydroxypropane-1,2,3-tricarboxylate;
49. 1-methyl-1-(2-oxo-2-((2R,3R,5R,6R)-3,4,5-trihydroxy-2,6-bis(hydroxymethyl)piperidin-1-yl)ethyl)guanidine-hemi(2-hydroxypropane-1,2,3-tricarboxylate);
50. tris(1-methyl-1-(2-oxo-2-((2R,3R,5R,6R)-3,4,5-trihydroxy-2,6-bis(hydroxymethyl)piperidin-1-yl)ethyl)guanidine)-2-hydroxypropane-1,2,3-tricarboxylate;
51. 1-methyl-1-(2-oxo-2-((2R,3R,5R,6R)-3,4,5-trihydroxy-2,6-bis(hydroxymethyl)piperidin-1-yl)ethyl)guanidine maleate;
52. 1-methyl-1-(2-oxo-2-((2R,3R,5R,6R)-3,4,5-trihydroxy-2,6-bis(hydroxymethyl)piperidin-1-yl)ethyl)guanidine hemimaleate;
53. 1-methyl-1-(2-oxo-2-((2R,3R,5R,6R)-3,4,5-trihydroxy-2,6-bis(hydroxymethyl)piperidin-1-yl)ethyl)guanidine malate;
54. 1-methyl-1-(2-oxo-2-((2R,3R,5R,6R)-3,4,5-trihydroxy-2,6-bis(hydroxymethyl)piperidin-1-yl)ethyl)guanidine hemimalate;
55. 1-methyl-1-(2-oxo-2-((2R,3R,5R,6R)-3,4,5-trihydroxy-2,6-bis(hydroxymethyl)piperidin-1-yl)ethyl)guanidine fumarate;
56. 1-methyl-1-(2-oxo-2-((2R,3R,5R,6R)-3,4,5-trihydroxy-2,6-bis(hydroxymethyl)piperidin-1-yl)ethyl)guanidine hemifumarate;
57. 1-methyl-1-(2-oxo-2-((2R,3R,4S,5S,6R)-3,4,5-trihydroxy-2,6-bis(hydroxymethyl)piperidin-1-yl)ethyl)guanidine hydrochloride;
58. 1-methyl-1-(2-oxo-2-((2R,3R,4S,5S,6R)-3,4,5-trihydroxy-2,6-bis(hydroxymethyl)piperidin-1-yl)ethyl)guanidine hydrobromide;

59. 1-methyl-1-(2-oxo-2-((2R,3R,4S,5S,6R)-3,4,5-trihydroxy-2,6-bis(hydroxymethyl)piperidin-1-yl)ethyl)guanidine sulfate;
60. 1-methyl-1-(2-oxo-2-((2R,3R,4S,5S,6R)-3,4,5-trihydroxy-2,6-bis(hydroxymethyl)piperidin-1-yl)ethyl)guanidine hemisulfate;
61. 1-methyl-1-(2-oxo-2-((2R,3R,4S,5S,6R)-3,4,5-trihydroxy-2,6-bis(hydroxymethyl)piperidin-1-yl)ethyl)guanidine 2,2,2-trifluoroacetate;
62. 1-methyl-1-(2-oxo-2-((2R,3R,4S,5S,6R)-3,4,5-trihydroxy-2,6-bis(hydroxymethyl)piperidin-1-yl)ethyl)guanidine 2-hydroxypropane-1,2,3-tricarboxylate;
63. 1-methyl-1-(2-oxo-2-((2R,3R,4S,5S,6R)-3,4,5-trihydroxy-2,6-bis(hydroxymethyl)piperidin-1-yl)ethyl)guanidine hemi(2-hydroxypropane-1,2,3-tricarboxylate);
64. tris(1-methyl-1-(2-oxo-2-((2R,3R,4S,5S,6R)-3,4,5-trihydroxy-2,6-bis(hydroxymethyl)piperidin-1-yl)ethyl)guanidine) 2-hydroxypropane-1,2,3-tricarboxylate;
65. 1-methyl-1-(2-oxo-2-((2R,3R,4S,5S,6R)-3,4,5-trihydroxy-2,6-bis(hydroxymethyl)piperidin-1-yl)ethyl)guanidine maleate;
66. 1-methyl-1-(2-oxo-2-((2R,3R,4S,5S,6R)-3,4,5-trihydroxy-2,6-bis(hydroxymethyl)piperidin-1-yl)ethyl)guanidine hemimaleate;
67. 1-methyl-1-(2-oxo-2-((2R,3R,4S,5S,6R)-3,4,5-trihydroxy-2,6-bis(hydroxymethyl)piperidin-1-yl)ethyl)guanidine malate;
68. 1-methyl-1-(2-oxo-2-((2R,3R,4S,5S,6R)-3,4,5-trihydroxy-2,6-bis(hydroxymethyl)piperidin-1-yl)ethyl)guanidine hemimalate;
69. 1-methyl-1-(2-oxo-2-((2R,3R,4S,5S,6R)-3,4,5-trihydroxy-2,6-bis(hydroxymethyl)piperidin-1-yl)ethyl)guanidine fumarate; and
70. 1-methyl-1-(2-oxo-2-((2R,3R,4S,5S,6R)-3,4,5-trihydroxy-2,6-bis(hydroxymethyl)piperidin-1-yl)ethyl)guanidine hemifumarate.

The non-limiting examples given above provide examples of creatine imino sugar amides salts which are within the present invention. One of skill in the art may readily envision various other salts within the scope of the present invention, considering the examples with reference to the specification herein provided. The following examples given below describe feasible methods for the production of creatine imino sugar amide salts of the present invention.

Also provided below is a method for producing creatine imino sugar amide salts of the present invention. Provided with the present specification, those of skill in the art will readily appreciate that certain modifications and variations may be made in the process of "scaling-up" the reaction to manufacture larger batches of creatine imino sugar amide salts which may be required or useful for commercial uses and supply requirements. Other methods of synthesis may also be apparent to those of skill in the art.

Furthermore, it would be known by one of skill in the art that varying the stoichiometric ratios of the various creatine imino sugar amides to the inorganic or organic acids will results in various salts. For example using equimolar ratios of creatine deoxynojirimycin amide and malic acid will lead to creatine deoxynojirimycin amide malate, whereas using 2 molar equivalents of creatine deoxynojirimycin amide for every 1 molar equivalent of malic acid will lead to creatine deoxynojirimycin amide hemimalate.

EXAMPLES

Example 1

552.58 g (2 mol) of creatine deoxynojirimycin amide is dissolved into 400 mL of hot ethanol, solution 1. Concurrently, 134.09 g (1 mol) of malic acid is dissolved in 200 mL of hot ethanol, solution 2. Solution 2 is added to solution 1 with stirring and the resultant combined solution is heated to the boiling point. If there are solids still present the combined solution is filtered at this temperature to remove unreacted starting materials. The combined solution is then allowed to cool to room temperature and then covered and refrigerated to allow crystallization to complete; about 24 hours. The resultant crystals are filtered under vacuum and washed with ice cold ethanol, yielding the creatine deoxynojirimycin amide hemimalate.

Example 2

552.58 g (2 mol) of creatine deoxygalactonojirimycin amide is dissolved into 400 mL of hot propanol, solution 1. Concurrently, 116.07 g (1 mol) of fumaric acid is dissolved in 200 mL of hot propanol, solution 2. Solution 2 is added to solution 1 with stirring and the resultant combined solution is heated to the boiling point. If there are solids still present the combined solution is filtered at this temperature to remove unreacted starting materials. The combined solution is then allowed to cool to room temperature and refrigerated to allow crystallization to complete; about 24 hours. The resultant crystals are filtered under vacuum and washed with ice cold ethanol, yielding the creatine deoxygalactonojirimycin amide hemifumarate.

Example 3

828.27 g (3 mol) of creatine deoxymannojirimycin amide is dissolved into 600 mL of hot isopropanol, solution 1. Concurrently, 192.12 g (1 mol) of citric acid is dissolved in 300 mL of hot isopropanol, solution 2. Solution 2 is added to solution 1 with stirring and the resultant combined solution is heated to the boiling point. If there are solids still present the combined solution is filtered at this temperature to remove unreacted starting materials. The combined solution is then allowed to cool to room temperature and refrigerated to allow crystallization to complete; about 24 hours. The resultant crystals are filtered under vacuum and washed with ice cold ethanol, yielding the tris(creatine deoxymannojirimycin amide) citrate.

Extensions and Alternatives

In the foregoing specification, the invention has been described with respect to specific embodiments thereof; however, it will be evident to one skilled in the art that various modifications and changes may be made thereto without departing from the scope of the invention.

All publications which are cited herein are hereby specifically incorporated by reference into the disclosure for the teachings for which they are cited.

What is claimed:

1. A composition comprising at least one salt of a creatine imino sugar amide said creatine imino sugar amide having a structure corresponding to Formula 1:

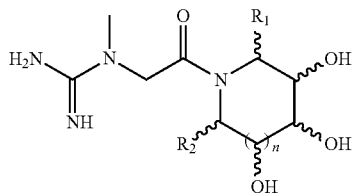

Formula 1 where R1=H, OH, or CH2OH;
R2=H OH, CH3 or CH2OH; and
n=0, 1 or 2.

2. The composition of claim 1, wherein the salt is an acid-addition salt of a creatine imino sugar amide with an inorganic or organic acid is selected from the group consisting of hydrochloric acid, hydrobromic acid, sulphuric acid, trifluoroacetic acid, citric acid, maleic acid, malic acid and fumaric acid.

3. The composition of claim 1, wherein the creatine imino sugar amide is selected from the group consisting of 1-methyl-1-(2-oxo-2-((2R,3R,4R,5S)-3,4,5-trihydroxy-2-(hydroxymethyl)piperidin-1-yl)ethyl)guanidine, 1-methyl-1-(2-oxo-2-((3S,4R,5S)-3,4,5-trihydroxy-2-(hydroxymethyl) piperidin-1-yl)ethyl)guanidine, 1-methyl-1-(2-oxo-2-((2R,3R,4R,5R)-3,4,5-trihydroxy-2-(hydroxymethyl)piperidin-1-yl)ethyl)guanidine, 1-methyl-1-(2-oxo-2-((2R,3R,5R,6R)-3,4,5-trihydroxy-2,6-bis(hydroxymethyl)piperidin-1-yl)ethyl) guanidine, and 1-methyl-1-(2-oxo-2-((2R,3R,4S,5S,6R)-3,4,5-trihydroxy-2,6-bis(hydroxymethyl)piperidin-1-yl)ethyl) guanidine.

4. The composition of claim 1, wherein the salt is a mono-creatine imino sugar amide salt.

5. The composition of claim 1, wherein the salt is a di-creatine imino sugar amide salt.

6. The composition of claim 1, wherein the salt is a tri-creatine imino sugar amide salt.

7. The composition of claim 1, further comprising at least one pharmaceutically acceptable carrier or diluent.

8. The composition of claim 7, wherein the composition is provided to a subject in an acceptable oral dosage form.

9. The composition of claim 7, wherein the composition is administered to a subject parentarally.

10. The composition of claim 8, wherein the acceptable oral dosage form is selected from the group consisting of a powder beverage mix, a liquid beverage, a ready-to-eat bar, a capsule, a liquid capsule, a tablet, a caplet, a dietary gel, a Soft-gel™ caplet, and a gel-cap.

* * * * *